US008865728B2

(12) United States Patent
Godessart Marina et al.

(10) Patent No.: US 8,865,728 B2
(45) Date of Patent: Oct. 21, 2014

(54) COMBINATIONS COMPRISING METHOTREXATE AND DHODH INHIBITORS

(75) Inventors: Nuria Godessart Marina, Barcelona (ES); Maria Pilar Pizcueta Lalanza, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 12/999,698

(22) PCT Filed: Jun. 18, 2009

(86) PCT No.: PCT/EP2009/004404
§ 371 (c)(1),
(2), (4) Date: Dec. 17, 2010

(87) PCT Pub. No.: WO2009/153043
PCT Pub. Date: Dec. 23, 2009

(65) Prior Publication Data
US 2011/0129445 A1    Jun. 2, 2011

(30) Foreign Application Priority Data
Jun. 20, 2008    (EP) ................................. 08382022

(51) Int. Cl.
A01N 43/90      (2006.01)
A61K 31/59      (2006.01)
A61K 31/455     (2006.01)
A61K 31/519     (2006.01)
A61K 45/06      (2006.01)

(52) U.S. Cl.
CPC ............. *A61K 45/06* (2013.01); *A61K 31/455* (2013.01); *A61K 31/519* (2013.01)
USPC .................... 514/262.1; 514/249; 424/145.1; 424/144.1

(58) Field of Classification Search
USPC ................. 424/85, 145.1, 144.1; 514/249
See application file for complete search history.

(56) References Cited

U.S. PATENT DOCUMENTS

| 5,780,592 | A  | 7/1998  | Müllner et al. |
| 7,071,222 | B2 | 7/2006  | Bartlett et al. |
| 7,258,118 | B2 | 8/2007  | Goede et al. |
| 8,501,943 | B2 | 8/2013  | Garcia Gonzalez |
| 8,536,165 | B2 | 9/2013  | Castro Palomino Laria et al. |
| 8,598,363 | B2 | 12/2013 | Boix Bernardini |
| 2003/0004171 | A1 | 1/2003 | Humphrey et al. |
| 2006/0081246 | A1 | 4/2006 | Goede et al. |
| 2010/0074898 | A1 | 3/2010 | Castro Palomino Laria et al. |
| 2011/0212945 | A1 | 9/2011 | Castro Palomino Laria et al. |
| 2011/0280831 | A1 | 11/2011 | Godessart Marina et al. |
| 2012/0003183 | A1 | 1/2012 | Garcia Gonzales et al. |
| 2012/0003184 | A1 | 1/2012 | Garcia Gonzales et al. |
| 2012/0014918 | A1 | 1/2012 | Perez Garcia et al. |
| 2012/0245359 | A1 | 9/2012 | Boix Bernardini |
| 2014/0005178 | A1 | 1/2014 | Castro Palomino Laria et al. |

FOREIGN PATENT DOCUMENTS

| EP | 0 780 128     | 6/1997  |
| WO | WO 97/34600   | 1/1997  |
| WO | WO 97/00703   | 9/1997  |
| WO | WO 99/45926   | 9/1999  |
| WO | WO 00/76489   | 12/2000 |
| WO | WO 02/080897  | 10/2002 |
| WO | WO 03/000325  | 1/2003  |
| WO | WO 03/006425  | 1/2003  |
| WO | WO 03/061742  | 7/2003  |
| WO | WO 2004/048314 | 6/2004 |
| WO | WO 2004/056746 | 7/2004 |
| WO | WO 2004/056747 | 7/2004 |
| WO | WO 2005/075410 | 8/2005 |
| WO | WO 2006/001961 | 1/2006 |
| WO | WO 2006/022442 | 3/2006 |
| WO | WO 2006/044741 | 4/2006 |
| WO | WO 2006/122788 | 11/2006 |
| WO | WO 2008/068041 | 6/2008 |
| WO | WO 2008/077639 | 7/2008 |
| WO | WO 2008/097180 | 8/2008 |
| WO | WO 2009/021696 | 2/2009 |
| WO | WO 2010/083975 | 7/2010 |
| WO | WO 2010/102824 | 9/2010 |
| WO | WO 2010/102825 | 9/2010 |
| WO | WO 2010/102826 | 9/2010 |
| WO | WO 2011/045059 | 4/2011 |

OTHER PUBLICATIONS

Cutolo et al, Ann Rheum Dis 2001 50: 729-735.*
Wahl et al, J. Clin. Invest. vol. 101, No. 5, Mar. 1998, 1163-1174.*
International Search Report for International Application No. PCT/EP2009/004404, dated Jul. 31, 2009.
Kremer, JM et al. "Concomitant Leflunomide Therapy in Patients with active Rheumatoid arthritis despite stable doses of Methotrexate," *Annals of Internal Medicine*, 137(9): 726-733, Nov. 5, 2002.
Weinblatt, ME et al. "Pharmacokinetics, safety, and efficacy of combination treatment with methotrexate and leflunomide in patients with active rheumatoid arthritis," *Arthritis & Rheumatism*, 42(7): 1322-1328, Jul. 1999.
U.S. Appl. No. 12/520,237, filed Sep. 9, 2009, Castro Palomino Laria et al.
U.S. Appl. No. 12/672,725, filed Mar. 16, 2010, Castro Palomino Laria et al.
U.S. Appl. No. 13/145,628, filed Jul. 21, 2011, Godessart Marina et al.
U.S. Appl. No. 13/256,104, filed Sep. 19, 2011, Garcia Gonzales et al.
U.S. Appl. No. 13/256,127, filed Sep. 19, 2011, Garcia Gonzales et al.
U.S. Appl. No. 13/256,349, filed Sep. 28, 2011, Perez Garcia et al.
U.S. Appl. No. 13/501,847, filed Jun. 12, 2012, Boix Bernardini et al.
Batt, DG, "Inhibitors of dihydroorotate dehydrogenase," *Expert Opinion on Therapeutic Patents*, 9(1):41-54 (1999).
Baughman, RP et al., "Leflunomide for chronic sarcoidosis," *Clinical Research*, 21: 43-48 (2004).

(Continued)

Primary Examiner — Wu-Cheng Winston Shen
Assistant Examiner — Jean Cornet
(74) Attorney, Agent, or Firm — Finnegan, Henderson, Farabow, Garrett & Dunner, LLP

(57) ABSTRACT

The present disclosure relates to combinations comprising (a) methotrexate, and (b) a DHODH inhibitor and their uses.

17 Claims, No Drawings

(56) References Cited

OTHER PUBLICATIONS

Berge, S.M. et al., "Pharmaceutical salts," *Journal of Pharmaceutical Science, American Pharmaceutical Association*, Washington, DC, 66(1):1-19, XP00562636, ISSN: 0022-3549 (1977).
Breedveld, FC et al., "Leflunomide: mode of action in the treatment of rheumatoid arthritis," *Annals of the Rheumatic Diseases*, 59: 841-849 (2000).
ClinialTrials.gov Identifier: NCT00637819, Sanofi-Aventis, Double blind, randomized, placebo controlled pilot study of leflunomide in systemic lupus erythematosus (SLE) (2008).
Dexter, DL et al., "Activity of a novel 4-quinolinecarboxylic acid, NSC 368390 [6-Fluoro-2-(2'-fluoro-1,1'-biphenyl-4-yl)-3-methyl-4-quinolinecarboxylic acid sodium salt], against experimental tumors," *Cancer Research*, 45:5563-5568 (1985).
Dimitrova, P. et al., "Restriction of de novo primidine biosynthesis inhibits Th1 cell activation and promotes Th2 cell differentiation," *The Journal of Immunology*, 169:3392-3399 (2002).
English-language Derwent Abstract for WO 06/022442.
Fox, RI, "Mechanism of action of leflunomide in rheumatoid arthritis," *The Journal of Rheumatology*, 25(53):20-26 (1998).
Gu, L. et al., "Preformulation salt selection. physical property comparisons of the tris (hydroxymethyl) aminomethane (THAM) salts of four analgesic/anti-inflammatory agents with the sodium salts and the free acids," *Pharmaceutical Research, Kluwer Academic Publishers*, 4(3):255-257, XP002099348, ISSN: 0724-8741 (1987).
Haibel, J. et al., "Six month open label trial of leflunomide in active ankylosing spondylitis," *Annals of the Rheumatic Diseases*, 64: 124-126 (2005).
International Search Report mailed May 8, 2008, for International Application No. PCT/EP2007/011401 (WO 2008/077639 A1).
International Search Report mailed Oct. 20, 2008, for International Application No. PCT/EP2008/006573 (WO 2009/021696).
International Search Report mailed Apr. 16, 2010, for International Application No. PCT/EP2010/000270 (WO 2010/083975).
International Search Report for International Application No. PCT/EP2010/001549 dated May 31, 2010.
International Search Report for International Application No. PCT/EP2010/001548 dated Nov. 18, 2010.
International Search Report for International Application No. PCT/EP2010/001550 mailed Apr. 23, 2010.
International Search Report for International Application No. PCT/EP2010/006283.
John, GT et al., "Leflunomide therapy for cytomegalovirus disease in renal allograft recipients," *Transplantation*, 77(9):1460-1461 (2003).
Kermack, WO, "Some Anilinopyridine Derivatives," *Journal of the Chemical Society*, pp. 726-727 (1942).
Kremer, JM, "Methotrexate and leflunomide: biochemical basis for combination therapy in the treatment of rheumatoid arthritis," *Seminars in Arthritis and Rheumatism*, 29(1):14-26 (1999).
Kulkarni, OP et al., "4SC-101, a novel small molecule dihydroorotate dehydrogenase inhibitor, suppresses systemic lupus erythematosus in MRL-(Fas)lpr mice," *The American Journal of Pathology*, 176(6):2840-2847 (2010).
Leban, J. et al., "Biphenyl-4-ylcarbamoyl thiophene carboxylic acids as potent DHODH inhibitors," *Bioorganic & Medicinal Chemistry Letters*, 16(2):267-270 (2006).
Liu, S. et al., "Structures of human dihydroorotate dehydrogenase in complex with antiproliferative agents," *Structure*, 8(1):25-33 (2000).
Löffler, M. et al., "Dihydroorotat-ubiquinone oxidoreductase links mitochondria in the biosynthesis of pyrimidine nucleotides," *Molecular and Cellular Biochemistry*, 174:125-129 (1997).
Majithia, V. et al., "Successful treatment of sarcoidosis with leflunomide," *Rheumatology*, 42:700-702 (2003).
Manna, SK et al., "Leflunomide suppresses TNF-induced cellular responses: effects on NF-{kappa}B, activator protein-1, c-Jun N-terminal protein kinase, and apoptosis," *Journal of Immunology*, 165:5962-5969 (2000).
McRobert, L. et al., "RNA interference (RNAi) inhibits growth of *Plasmodium falciparum*," *Molecular & Biochemical Parasitology*, 19: 273-278 (2002).
Mehta, V. et al., "Leflunomide," *Indian J. Dermatol. Venereol. Leprol.*, 75(4):422-425 (2009).
Metzler, C. et al., "Maintenance of remission with leflunomide in wegener's granulomatosis," *Rheumatology*, 43:315-320 (2004).
Miyaura, N. et al., "Palladium-catalyzed cross-coupling reactions of organoboron compounds," *Chemical Reviews*, 35:2457-2483 (1995).
Notice of Allowance dated May 2, 2012, in U.S. Appl. No. 12/520,237.
O'Connor, PW et al., "A phase II study of the safety and efficacy of teriflunomide in multiple sclerosis with relapses," *Neurology*, 66:894-900 (2006).
Office Action dated Feb. 28, 2011, in U.S. Appl. No. 12/520,237.
Office Action dated Jun. 12, 2012, in U.S. Appl. No. 12/672,725.
Office Action dated Jun. 2, 2011, in U.S. Appl. No. 12/520,237.
Office Action dated Nov. 4, 2011, in U.S. Appl. No. 12/520,237.
Phillips, Margaret A. et al., "Triazolopyrimidine-based dihydroorotate dehydrogenase inhibitors with potent and selective activity against the malaria parasite *Plasmodium falciparum*", *J. Med. Chem.*, 51:3649-3653 (2008).
Sanders, S. et al., "Leflunomide for the treatment of rheumatoid arthritis and autoimmunity," *American Journal of the Medical Sciences*, 323(4):190-193 (2002).
Schläpfer, E. et al., "Anti-HIV-1 activity of leflunomide: a comparison with mycophenolic acid and hydroxyurea," *AIDS*, 17(11):1613-1620 (2003).
Silverman, E. et al., "Long-term open-label preliminary study of the safety and efficacy of leflunomide in patients with polyarticular-course juvenile rheumatoid arthritis," *Arthritis & Rheumatism*, 52(2):554-562 (2005).
Silverman, RB, "The organic chemistry of drug design and drug action," Chapter 2, Section 2.2, pp. 29-32, Elsevier Academic Press (2004).
Spano, R. et al., "Preparation and pharmacology of some derivatives of 2-aminonicotinic," *Farmaco, Edizione Scientifica, Societa Chimica Italiana*, Pavia, IT, 26(9):844-849 (1971).
English Language Caplus Abstract for Spano, R. et al. "Preparation and pharmacology of some derivatives of 2-aminonicotinic," *Farmaco, Edizione Scientifica*, Societa Chimica Italiana, Pavia, IT, 26(9): 844-849 (1971).
Stahl, P.H. et al., "Tromethamine", *Handbook of Pharmaceutical Salts Properties, Selection and Use*, pp. 324-325, XP002214621 (2002).
Tlacuilo Parra, JA et al., "Leflunomide in the treatment of psoriasis: results of a phase II open trial," *British Journal of Dermatology*, 150: 970-976 (2004).
Urushibara, M. et al., "The antirheumatic drug leflunomide inhibits osteoclastogenesis by interferingwith receptor activator of NF-$_K$B ligand-stimulated induction of nuclear factor of activated T cells c1," *Arthritis & Rheumatism*, 50(3):794-804 (2004).
Vyas, V.K. et al., "Recent developments in the medicinal chemistry and therapeutic potential of dihydroorotate dehydrogenase (DHODH) inhibitors", *Mini-Reviews in Medicinal Chemistry*, 11:1039-1055 (2011).
Ando et al., in Remington: The Science and Practice of Pharmacy. 20th Edition. Alfonso R. Gennaro (Ed.). Philadelphia, PA: Lippincott Williams & Wilkins, 2000; pp. 704-712.
Bastin, R.J. et al., "Salt Selection and Optimisation Procedures for Pharmaceutical New Chemical Entities" Organic Process Research & Development (2000) 4:427-435.
Grigoreva, "Catalytic Activity," Khimiko-Farmatsevticheskii Zhurnal, 12(4): 7-14 (1978).
English translation of Grigoreva, "Catalytic Activity," Khimiko-Farmatsevticheskll Zhurnal (1978) 12(4):7-14.
Morissette, S.L. et al. "High-throughput crystallization: polymorphs, salts, co-crystals and solvates of pharmaceutical solids," Advanced Drug Delivery Reviews, 56:275-300 (2004).
Mroczkowski, P.J. et al., "Methotrexate and leflunornide combination therapy for patients with active rheumatoid arthritis", Clin. Exp. Rheumatol, 1999, 17(Suppl. 18): S66-S68.

(56) References Cited

OTHER PUBLICATIONS

Notice of Allowability (Corrected) dated Jun. 26, 2012, in U.S. Appl. No. 12/520,237.
Notice of Allowance dated May 1, 2013, in U.S. Appl. No. 13/256,127.
Office Action (Restriction Requirement) dated Sep. 13, 2012, in U.S. Appl. No. 13/145,628.
Office Action dated Jul. 30, 2012, in U.S. Appl. No. 12/672,725.
Office Action (Restriction Requirement) dated Jun. 14, 2012, in U.S. Appl. No. 13/256,127.
Office Action dated Sep. 21, 2012, in U.S. Appl. No. 13/256,127.
Office Action (Restriction Requirement) dated Apr. 2, 2013, in U.S. Appl. No. 13/567,437.
Office Action (Restriction Requirement) dated Apr. 12, 2013, in U.S. Appl. No. 13/256,349.
Patani et al., "Bioisoterism: A Rational Approach in Drug Design," Chem. Rev. 1996, 3147-3176.
Saag, K et al. "American College of Rheumatology 2008 Recommendations for the Use of Nonbiologic and Biologic Disease-Modifying Antirheumatic Drugs in Rheumatoid Arthritis" Arthritis & Rheumatism 59 (6), 762-784 (2008).
Silverman, RB "The Organic Chemistry of Drug Design and Drug Action," Section 2.1, pp. 9. Elsevier Academic Press (2004).
Swierkot, Jerzy et al., Methotrexate in rheumatoid arthritis, Pharmacological Reports, Institute of Pharmacology Polish Academy of Science, 2006, 56, 473-492.
Vippagunta, S.R. et al. "Crystalline Solids," Advanced Drug Delivery Reviews, 48:3-26 (2001).
Office Action dated Sep. 23, 2013, in U.S. Appl. No. 13/256,104.
F. Zaragoza Dörwald, Side Reactions in Organic Synthesis: A Guide to Successful Synthesis Design, Weinheim: Wiley-VCH Verlag GmbH & Co. KGaA, 2005, Preface.
V. Craig Jordan, "Tamoxifen: A most unlikely pioneering medicine," Nature Reviews: Drug Discovery vol. 2, 2003, pp. 205-213.
Office Action dated Jan. 9, 2014, in U.S. Appl. No. 13/256.349.
Office Action dated Feb. 19, 2014 in U.S. Appl. No. 13/145,628.
Office Action dated Mar. 11, 2014, in U.S. Appl. No. 13/256,104.
U.S. Appl. No. 13/964,181.
Cecil Textbook of Medicine, edited by Bennet, J.C., and Plum F., 20$^{th}$ edition, vol. 1, 1004-1010, 1996.
David et al., "Impact of the counterion on the solubility and physicochemical properties of salts of carboxylic acid acid drugs," Drug Development and Industrial Pharmacy, 2012; 38(1):93-103.
Dermer et al., "Another Anniversary for the War on Cancer" Bio/Technology, 1994, 12:320.
Golub et al., "Molecular Classification of Cancer: Class Discovery and Class Prediction by Gene Experssion Monitoring." Science, 286, 531-537, 1999.
Freshney et al., Culture of Animal Cells, A Manual of Basic Technique, Alan R. Liss, Inc., 1983, New York, p. 4.
Notice of Allowance dated Nov. 26, 2013, in U.S. Appl. No. 13/567,437.
Notice of Allowance dated Aug. 8, 2013, in U.S. Appl. No. 13/501,847.
O'Connor et al., "Preparation and characterization of a range of diclolfenac salts," International Journal of Pharmaceutics, vol. 266, 163-179 (2001).
Office Action (Restriction Requirement) dated May 9, 2013, in U.S. Appl. No. 13/501,847.
Office Action dated May 17, 2013, in U.S. Appl. No. 13/567,437.
Office Action dated May 30, 2013, in U.S. Appl. No. 13/145,628.
Office Action dated Jun. 11, 2013, in U.S. Appl. No. 13/256,349.
Office Action dated Jan. 9, 2014, in U.S. Appl. No. 13/256,349.

\* cited by examiner

COMBINATIONS COMPRISING METHOTREXATE AND DHODH INHIBITORS

This application is a national stage filing under 35 U.S.C. §371 of International Application No. PCT/EP2009/004404 filed on 18 Jun. 2009, which claims priority of European Patent Application No. 08382022.5, filed on 20 Jun. 2008. The contents of both applications are incorporated herein by reference.

The present invention relates to new combinations of methotrexate with DHODH inhibitors. These combinations are useful in the treatment, prevention or suppression of diseases and disorders known to be susceptible to improvement with methotrexate and/or by inhibition of dihydroorotate dehydrogenase, such as autoimmune diseases, immune and inflammatory diseases, destructive bone disorders, malignant neoplastic diseases, angiogenic-related disorders, viral diseases, and infectious diseases.

BACKGROUND OF THE INVENTION

Methotrexate (MTX) is an antimetabolite and immunomodulator that affects many intracellular pathways of purine metabolism. It is effective in reducing the signs and symptoms of rheumatoid arthritis (RA), as well as in slowing or halting radiographic damage. Due to its efficacy, ease of administration and relatively low cost, MTX has become the first-line oral therapy in most patients with RA. In those patients who have an incomplete response to MTX, another DMARD (disease modifying anti-rheumatic drug) is added on top of it. Thus, combination therapy with MTX is more and more frequent in the clinical practice.

Leflunomide is an example of such a DMARD. It was approved in September 1998 for use in RA. It has been shown to reduce the signs and symptoms of the disease, to inhibit structural damage (evidenced by X-ray erosions and joint space narrowing) and to improve physical function. Teriflunomide is the active metabolite of Leflunomide.

Methotrexate is thought to act primarily on purine pathways of cellular metabolism, whereas Leflunomide affects pyrimidine pathways. Given the diverse intracellular pathways affected by both drugs, the combination of Leflunomide and methotrexate has the potential for biochemical synergy. In fact, it has been reported that the combination of both agents led to considerable clinical improvement (see for example, Weinblatt M E et al. "*Pharmacokinetics, safety, and efficacy of combination treatment with methotrexate and leflunomide in patients with active rheumatoid arthritis*". Arthritis Rheum 1999; 42 (7): 1322-8 and Kremer J M et al. "*Concomitant Leflunomide therapy in patients with active rheumatoid arthritis despite stable doses of methotrexate*". Ann. Intern. Med., 2002; 137, 726-733).

Unfortunately, both methotrexate and leflunomide have serious adverse effects, in particular hepatotoxicity. Methotrexate may cause fatal liver damage such as fibrosis and cirrhosis after prolonged use. Liver enzyme increases are frequently seen during treatment with methotrexate. Hence, regular and careful monitoring of patients taking MTX is essential, particularly when MTX is combined with other DMARDs.

The most common reported adverse events of Leflunomide include diarrhoea, dyspepsia, rash, hair loss, hypertension and elevated hepatic enzymes. The hepatotoxicity potential is of special relevance and regular laboratory tests, including blood tests of liver function, must be performed for all patients taking this medication. Leflunomide is not recommended for use in patients with evidence of hepatitis B or C infection or significant hepatic impairment.

Clinical trials have reported that the number of patients experiencing an increase in liver markers (measured as transaminase levels) is notably higher in the group of Leflunomide plus MTX than in the group of MTX alone. The product information for Leflunomide warns against combination with methotrexate on the basis that such combination therapy can lead to additive or even synergistic hepatotoxicity.

The mechanism responsible for the hepatotoxicity of leflunomide, and in particular of its active metabolite, teriflunomide, is unknown, but it has been attributed to its activity as inhibitor of dihydroorotate dehydrogenase (DHODH). Liver toxicity has thus been identified as an adverse effect directly derived from the mechanism of action of DHODH-inhibitors, which has hampered the development of this class of compounds.

DESCRIPTION OF THE INVENTION

We have now found that, contrary to general belief, the inhibition of DHODH is not responsible for the liver damage produced by leflunomide and that DHODH inhibitors are particularly suitable for combination with methotrexate.

It is known that inhibition of DHODH produces immunosuppressant and antiproliferative effects. DHODH inhibitors could therefore be used as immunosuppressants and as antiproliferatives in the treatment of autoimmune, inflammatory and proliferative diseases, like RA.

Our invention is based on the surprising finding that the inhibition of DHODH is not linked to hepatotoxicity and, consequently, DHODH inhibitors devoid of hepatotoxic potential represent an important contribution to the treatment of these diseases, thanks to their advantageous combinability with MTX, the most commonly used first-line drug in RA treatment.

We have developed an in vivo model of hepatotoxicity assessment in mice, in which test compounds are administered by intraperitoneal route to maximise liver exposure. In this model, Teriflunomide, the active metabolite of Leflunomide, has shown a drastic increase in the levels of transaminases and bilirrubin in plasma, whereas DHODH inhibitors do not show an increase in any of the plasma liver markers in the same model, while maintaining their efficacy in arthritis.

Thus, the present invention is directed to a combination product which comprises (a) Methotrexate and (b) and DHODH inhibitor, in particular a non-hepatotoxic DHODH inhibitor.

In a preferred embodiment the DHODH inhibitor is other than Leflunomide or any active metabolite thereof.

Most preferably, the DHODH inhibitor (b) is a compound of formula (I):

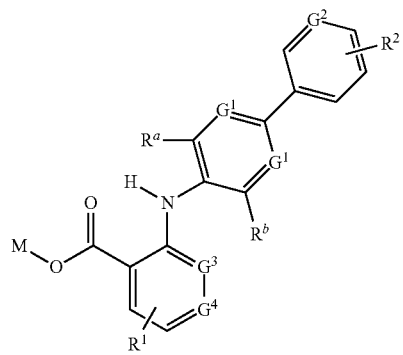

wherein
one of the groups $G^1$ represents a nitrogen atom or a group $CR^c$ and the other represents a group $CR^c$;
$G^2$ represents a nitrogen atom or a group $CR^d$;

$R^1$ represents a group selected from hydrogen atoms, halogen atoms, $C_{1-4}$ alkyl groups which may be optionally substituted by 1, 2 or 3 substituents selected from halogen atoms and hydroxy groups, and $C_{3-8}$ cycloalkyl groups which may be optionally substituted by 1, 2 or 3 substituents selected from halogen atoms and hydroxy groups;

$R^2$ represents a group selected from hydrogen atoms, halogen atoms, hydroxyl groups, $C_{1-4}$ alkyl groups which may be optionally substituted by 1, 2 or 3 substituents selected from halogen atoms and hydroxy groups, $C_{1-4}$ alkoxy groups which may be optionally substituted by 1, 2 or 3 substituents selected from halogen atoms and hydroxy groups, and $C_{3-8}$ cycloalkyl groups which may be optionally substituted by 1, 2 or 3 substituents selected from halogen atoms and hydroxy groups;

$R^a$, $R^b$ and $R^c$ independently represent groups selected from hydrogen atoms, halogen atoms, $C_{1-4}$ alkyl groups which may be optionally substituted by 1, 2 or 3 substituents selected from halogen atoms and hydroxy groups, and $C_{1-4}$ alkoxy groups which may be optionally substituted by 1, 2 or 3 substituents selected from halogen atoms and hydroxy groups;

$R^d$ represents a group selected from hydrogen atoms, halogen atoms, hydroxyl groups, $C_{1-4}$ alkyl groups which may be optionally substituted by 1, 2 or 3 substituents selected from halogen atoms and hydroxy groups, and $C_{1-4}$ alkoxy groups which may be optionally substituted by 1, 2 or 3 substituents selected from halogen atoms and hydroxy groups, and $C_{3-8}$ cycloalkoxy groups which may be optionally substituted by 1, 2 or 3 substituents selected from halogen atoms and hydroxy groups;

one of the groups $G^3$ and $G^4$ is a nitrogen atom and the other is a CH group;

M is a hydrogen atom or an pharmaceutically acceptable cation;

with the proviso that, when at least one of the groups $R^a$ and $R^b$ represent a hydrogen atom and $G^2$ is a group $CR^d$, then $R^d$ represents a groups selected from $C_{1-4}$ alkoxy groups which may be optionally substituted by 1, 2 or 3 substituents selected from halogen atoms and hydroxy groups, $C_{3-8}$ cycloalkoxy groups which may be optionally substituted by 1, 2 or 3 substituents selected from halogen atoms and hydroxy groups;

and the pharmaceutically acceptable salts and N-oxides thereof.

As used herein the term alkyl embraces optionally substituted, linear or branched hydrocarbon radicals having 1 to 4 carbon atoms. Preferred substituents on the alkyl groups are halogen atoms and hydroxy groups, and are more preferably halogen atoms.

Examples include methyl, ethyl, n-propyl, i-propyl, n-butyl, sec-butyl and tert-butyl radicals.

As used herein the term alkoxy embraces optionally substituted, linear or branched oxy-containing radicals each having 1 to 4 carbon atoms. Preferred substituents on the alkoxy groups are halogen atoms and hydroxy groups, and are more preferably halogen atoms.

Examples include methoxy, ethoxy, n-propoxy, i-propoxy, n-butoxy, sec-butoxy and tert-butoxy radicals.

As used herein, the term cycloalkyl embraces saturated carbocyclic radicals and, unless otherwise specified, a cycloalkyl radical typically has from 3 to 8 carbon atoms.

Examples include cyclopropyl, cyclobutyl, cyclopentyl, cyclohexyl and cycloheptyl. When a cycloalkyl radical carries 2 or more substituents, the substituents may be the same or different. Preferred substituents on the cycloalkyl groups are halogen atoms and hydroxy groups, and are more preferably halogen atoms.

As used herein, the term cycloalkoxy embraces saturated oxy-containing carbocyclic radicals and, unless otherwise specified, a cycloalkoxy radical typically has from 3 to 8 carbon atoms.

Examples include cyclopropyloxy, cyclobutyloxy, cyclopentyloxy, cyclohexyloxy and cycloheptyloxy. When a cycloalkoxy radical carries 2 or more substituents, the substituents may be the same or different. Preferred substituents on the cycloalkoxy groups are halogen atoms and hydroxy groups, and are more preferably halogen atoms.

As used herein, some of the atoms, radicals, moieties, chains or cycles present in the general structures of the invention are "optionally substituted". This means that these atoms, radicals, moieties, chains or cycles can be either unsubstituted or substituted in any position by one or more, for example 1, 2, 3 or 4, substituents, whereby the hydrogen atoms bound to the unsubstituted atoms, radicals, moieties, chains or cycles are replaced by chemically acceptable atoms, radicals, moieties, chains or cycles. When two or more substituents are present, each substituent may be the same or different.

As used herein, the term halogen atom embraces chlorine, fluorine, bromine or iodine atoms typically a fluorine, chlorine or bromine atom, most preferably bromine or fluorine. The term halo when used as a prefix has the same meaning.

M may be a hydrogen atom or a pharmaceutically acceptable cation. When M is a pharmaceutically acceptable cation, the compound represented by formula (I) may alternatively be represented by formula (I*) below.

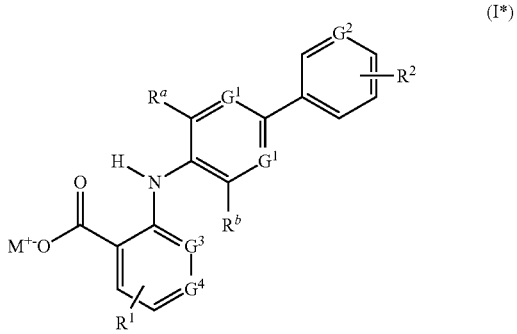

(I*)

As used herein, the term pharmaceutically acceptable cation embraces both inorganic cations, for example alkali metal cations ($Li^+$, $Na^+$, $K^+$), alkaline earth cations ($Ca^{2+}$, $Mg^{2+}$) and other pharmaceutically acceptable inorganic cations known in the art ($Zn^{2+}$, $Al^{3+}$), and organic cations, for example ammonium ion (i.e., $NH_4^+$) and substituted ammonium ions, such as $NH_3R^{1+}$, $NH_2(R^1)_2^+$, $NH(R^1)_3^+$ and $N(R^1)_4^+$, where each $R^1$ is independently selected from a phenyl group, a benzyl group, $C_{1-4}$ alkyl and $C_{3-8}$ cycloalkyl.

Examples of some suitable substituted ammonium ions are $EtNH_3^+$, $Et_2NH_2^+$, $Et_3NH^+$, $(C_6H_{11})_2NH_2^+$, $CH_3CH_2CH_2CH_2NH_3^+$, $PhCH_2NH_3^+$ and $(Ph)(PhCH_2)NH_2^+$. An example of a common quaternary ammonium ion is $N(CH_3)_4^+$.

Typically, M is a hydrogen atom or a pharmaceutically acceptable cation selected from $Li^+$, $Na^+$, $K^+$, $Ca^{2+}$ and $Mg^{2+}$. It is preferred that M is a hydrogen atom or a pharmaceutically acceptable cation selected from $Li^+$, $Na^+$ and $K^+$. More preferably M is a hydrogen atom or $Li^+$, and most preferred is when M is a hydrogen atom.

If M of formula (I) is a pharmaceutically acceptable cation having a charge greater than +1, then additional anions are present to maintain the electroneutrality of the compound. The counteranion may be an anion X— as defined below or an anion as represented in formula (I*) above.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic, cyclohexylsulfamic (cyclamic) or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

Other preferred salts according to the invention are quaternary ammonium compounds wherein an equivalent of an anion (X—) is associated with the positive charge of the N atom. X— may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate. X— is preferably an anion selected from chloride, bromide, iodide, sulphate, nitrate, acetate, maleate, oxalate, succinate or trifluoroacetate. More preferably X— is chloride, bromide, trifluoroacetate or methanesulphonate.

As used herein, an N-oxide is formed from the tertiary basic amines or imines present in the molecule, using a convenient oxidising agent.

Typically, $R^1$ is selected from the group consisting of hydrogen, bromine and fluorine atoms, methyl, ethyl, cyclopropyl and cyclobutyl.

Typically, $G^3$ represents a nitrogen atom and $G^4$ represents a group CH.

Typically, $G^3$ represents a group CH and $G^4$ represents a nitrogen atom.

Typically, $G^1$ represent a group $CR^c$.

Typically, each $R^c$ is independently selected from the groups consisting of hydrogen atoms, fluorine atoms, chlorine atoms and $C_{1-3}$ alkyl groups.

Typically, $G^2$ represents a group $CR^d$.

Typically, $R^d$ is selected from the groups consisting of hydroxy, $C_{1-3}$ alkoxy groups, 2,2,2-trifluoroethoxy and $C_{3-4}$ cycloalkoxy groups. Preferably, $C_{1-3}$ alkoxy groups, 2,2,2-trifluoroethoxy and $C_{3-4}$ cycloalkoxy groups.

Typically, $R^a$ is selected from the groups consisting of fluorine atoms, methyl groups and trifluoromethoxy groups.

Typically, $R^b$ is selected from the group consisting of hydrogen atoms, fluorine atoms and chlorine atoms.

Typically, $R^2$ is selected from the group consisting of hydrogen atoms and halogen atoms, preferably hydrogen atoms and fluorine atoms.

Typically, both groups $G^1$ represent $C(R^c)$ groups, $G^2$ represents a $C(R^d)$ group, preferably $G^2$ is a group selected from C(OH), C(OMe) and C(OEt); $R^a$ is a fluorine atom, $R^b$ is selected from the group consisting of hydrogen atoms and fluorine atoms and $R^1$ is selected from the group consisting of hydrogen, bromine and fluorine atoms, methyl, ethyl and cyclopropyl groups, Preferably, both $G^1$ represent CH groups, $G^2$ is a group selected from C(OMe) and C(OEt); $R^a$ is a fluorine atom, $R^b$ is selected from the group consisting of hydrogen atoms and fluorine atoms and $R^1$ is selected from the group consisting of hydrogen, bromine and fluorine atoms, methyl, ethyl and cyclopropyl groups.

Preferably, $R^c$ is a hydrogen atom, $R^d$ is a hydroxy or a $C_{1-3}$ alkoxy groups and $R^2$ is a hydrogen atom, preferably $R^c$ is a hydrogen atom, $R^d$ is a $C_{1-3}$ alkoxy and $R^2$ is a hydrogen atom.

Preferably, $G^3$ represents a nitrogen atom, $G^4$ represents a group CH and $R^b$ is a fluorine atom and the compounds wherein $G^3$ represents a group CH, $G^4$ represents a nitrogen atom.

More preferably, both groups $G^1$ represent $C(R^c)$ groups, $G^2$ represents $C(R^d)$ group, $R^a$ is a fluorine atom, $R^b$ is selected from the group consisting of hydrogen atoms and fluorine atoms and $R^1$ is selected from the group consisting of hydrogen, bromine and fluorine atoms, methyl, ethyl and cyclopropyl groups, Preferably $R^c$ is a hydrogen atom, $R^d$ is selected from the group consisting of $C_{1-3}$ alkoxy and $C_{3-4}$ cycloalkoxy groups and $R^2$ is a hydrogen atom. Particularly preferred are the compounds wherein $G^3$ represents a nitrogen atom, $G^4$ represents a group CH and $R^b$ is a fluorine atom and the compounds wherein $G^3$ represents a group CH, $G^4$ represents a nitrogen atom.

Preferably, the DHODH inhibitor is one of the following list:
1. 2-(3-Fluoro-3'-methoxybiphenyl-4-ylamino)nicotinic acid;
2. 2-(3'-Ethoxy-3-fluorobiphenyl-4-ylamino)nicotinic acid;
3. 2-(3-Fluoro-3'-(trifluoromethoxy)biphenyl-4-ylamino) nicotinic acid;
4. 2-(3'-Ethoxy-3-(trifluoromethoxy)biphenyl-4-ylamino) nicotinic acid;
5. 2-(3'-Methoxy-3-(trifluoromethoxy)biphenyl-4-ylamino) nicotinic acid;
6. 2-(2,5-Difluoro-3'-methoxybiphenyl-4-ylamino)nicotinic acid;
7. 2-(3'-Ethoxy-2,5-difluorobiphenyl-4-ylamino)nicotinic acid;
8. 2-(2',3-difluoro-3'-methoxybiphenyl-4-ylamino)nicotinic acid;
9. 2-(2-Methyl-3'-(trifluoromethoxy)biphenyl-4-ylamino) nicotinic acid;
10. 2-(3-Chloro-3'-(trifluoromethoxy)biphenyl-4-ylamino) nicotinic acid;
11. 2-(3-Chloro-3'-ethoxybiphenyl-4-ylamino)nicotinic acid;
12. 2-(3-Methyl-3'-(trifluoromethoxy)biphenyl-4-ylamino) nicotinic acid;
13. 2-(3-Chloro-3'-methoxybiphenyl-4-ylamino)nicotinic acid;
14. 2-(3'-(Difluoromethoxy)-3-fluorobiphenyl-4-ylamino) nicotinic acid;
15. 2-(3'-Cyclobutoxy-3-fluorobiphenyl-4-ylamino)nicotinic acid;
16. 2-(3-Fluoro-3'-(2,2,2-trifluoroethoxy)biphenyl-4-ylamino)nicotinic acid;
17. 2-(3'-Cyclobutoxy-3,5-difluorobiphenyl-4-ylamino) nicotinic acid;
18. 2-(3,5-Difluoro-3'-(trifluoromethoxy)biphenyl-4-ylamino)nicotinic acid;
19. 2-(3'-Ethoxy-3,5-difluorobiphenyl-4-ylamino)nicotinic acid;
20. 2-(3,5-Difluoro-3'-methoxybiphenyl-4-ylamino)nicotinic acid;
21. Lithium 3-(3'-ethoxy-3-fluorobiphenyl-4-ylamino)isonicotinate;

22. Lithium 3-(3-fluoro-3'-methoxybiphenyl-4-ylamino)isonicotinate;
23. Lithium 3-(3'-methoxy-3-(trifluoromethoxy)biphenyl-4-ylamino)isonicotinate;
24. Lithium 3-(3-fluoro-3'-(trifluoromethoxy)biphenyl-4-ylamino)isonicotinate;
25. 2-(3'-Ethoxybiphenyl-4-ylamino)nicotinic acid;
26. 2-(5-Fluoro-2-methyl-3'-(trifluoromethoxy)biphenyl-4-ylamino)nicotinic acid;
27. 2-(2',3-Difluoro-5'-isopropoxybiphenyl-4-ylamino)nicotinic acid;
28. 2-(3-Fluoro-3'-methoxybiphenyl-4-ylamino)-5-methylnicotinic acid;
29. 2-(3,5-Difluoro-3'-hydroxybiphenyl-4-ylamino)nicotinic acid;
30. 5-Bromo-2-(3-fluoro-3'-methoxybiphenyl-4-ylamino)nicotinic acid;
31. 5-Bromo-2-(3,5-difluoro-3'-methoxybiphenyl-4-ylamino)nicotinic acid;
32. 5-Bromo-2-(3-fluoro-3'-(trifluoromethoxy)biphenyl-4-ylamino)nicotinic acid;
33. 2-(3-Fluoro-3'-(trifluoromethoxy)biphenyl-4-ylamino)-5-methylnicotinic acid;
34. 5-Cyclopropyl-2-(3-fluoro-3'-methoxybiphenyl-4-ylamino)nicotinic acid;
35. 2-(3,5-Difluoro-3'-methoxybiphenyl-4-ylamino)-5-methylnicotinic acid;
36. 2-(3'-Ethoxy-5-fluoro-2-methylbiphenyl-4-ylamino)nicotinic acid;
37. 2-(5-Fluoro-3'-methoxy-2-methylbiphenyl-4-ylamino)nicotinic acid;
38. 2-(3'-ethoxy-3,5-difluorobiphenyl-4-ylamino)-5-methylnicotinic acid;
39. 5-cyclopropyl-2-(3'-ethoxy-3,5-difluorobiphenyl-4-ylamino)nicotinic acid;
40. 2-(3,5-difluoro-3'-methoxybiphenyl-4-ylamino)-5-ethylnicotinic acid;
41. 5-bromo-2-(3'-ethoxy-2,5-difluorobiphenyl-4-ylamino)nicotinic acid;
42. 5-cyclopropyl-2-(3'-ethoxy-2,5-difluorobiphenyl-4-ylamino)nicotinic acid;
43. 2-(5-fluoro-3'-methoxy-2-methylbiphenyl-4-ylamino)-5-methylnicotinic acid;
44. 5-cyclopropyl-2-(5-fluoro-3'-methoxy-2-methylbiphenyl-4-ylamino)nicotinic acid;
45. 2-(2',3,5-trifluoro-3'-methoxybiphenyl-4-ylamino)nicotinic acid;
46. 2-(2'-chloro-3,5-difluorobiphenyl-4-ylamino)nicotinic acid;
47. 2-(3'-cyclopropoxy-3,5-difluorobiphenyl-4-ylamino)nicotinic acid;
48. 2-(3,5-difluoro-2-methylbiphenyl-4-ylamino)nicotinic acid;
49. 5-cyclopropyl-2-(2,5-difluoro-3'-methoxybiphenyl-4-ylamino)nicotinic acid;
50. 2-(3'-cyclopropoxy-3,5-difluorobiphenyl-4-ylamino)-5-cyclopropylnicotinic acid;
51. 5-chloro-2-(3,5-difluoro-3'-methoxybiphenyl-4-ylamino)nicotinic acid;
52. 5-cyclopropyl-2-(3,5-difluoro-3'-(trifluoromethoxy)biphenyl-4-ylamino)nicotinic acid;
53. 2-(2,3,5-trifluoro-3'-methoxybiphenyl-4-ylamino)nicotinic acid;
54. 2-(2'-chloro-3,5-difluorobiphenyl-4-ylamino)-5-cyclopropylnicotinic acid;
55. 2-(3,5-difluoro-3'-methoxy-2-methylbiphenyl-4-ylamino)nicotinic acid;
56. 2-(3,5-difluoro-2-methyl-3'-(trifluoromethoxy)biphenyl-4-ylamino)nicotinic acid;
57. 2-(2'-chloro-3,5-difluoro-2-methylbiphenyl-4-ylamino)nicotinic acid;
58. 5-chloro-2-(3,5-difluorobiphenyl-4-ylamino)nicotinic acid;
59. 5-chloro-2-(2'-chloro-3,5-difluorobiphenyl-4-ylamino)nicotinic acid;
60. 2-(2,3,5,6-tetrafluoro-3'-methoxybiphenyl-4-ylamino)nicotinic acid;
61. 2-(3,5-difluoro-2'-methylbiphenyl-4-ylamino)nicotinic acid;
62. 3-(3'-cyclopropoxy-3-fluorobiphenyl-4-ylamino)isonicotinic acid;

or a pharmaceutically acceptable salt or N-oxide thereof.

More preferably, the DHODH inhibitor is one of:

2-(3'-Ethoxy-3-(trifluoromethoxy)biphenyl-4-ylamino)nicotinic acid;

2-(3'-Methoxy-3-(trifluoromethoxy)biphenyl-4-ylamino)nicotinic acid;

2-(3'-Ethoxy-3,5-difluorobiphenyl-4-ylamino)nicotinic acid;

2-(3,5-Difluoro-3'-methoxybiphenyl-4-ylamino)nicotinic acid;

Lithium 3-(3'-ethoxy-3-fluorobiphenyl-4-ylamino)isonicotinate;

Lithium 3-(3-fluoro-3'-methoxybiphenyl-4-ylamino)isonicotinate;

Lithium 3-(3'-methoxy-3-(trifluoromethoxy)biphenyl-4-ylamino)isonicotinate;

2-(3-Fluoro-3'-methoxybiphenyl-4-ylamino)-5-methylnicotinic acid;

5-Bromo-2-(3,5-difluoro-3'-methoxybiphenyl-4-ylamino)nicotinic acid;

5-Cyclopropyl-2-(3-fluoro-3'-methoxybiphenyl-4-ylamino)nicotinic acid;

2-(3,5-Difluoro-3'-methoxybiphenyl-4-ylamino)-5-methylnicotinic acid;

2-(3,5-difluoro-3'-methoxybiphenyl-4-ylamino)-5-ethylnicotinic acid;

2-(2'-chloro-3,5-difluorobiphenyl-4-ylamino)nicotinic acid;

2-(3'-cyclopropoxy-3,5-difluorobiphenyl-4-ylamino)nicotinic acid;

2-(3,5-difluoro-2-methylbiphenyl-4-ylamino)nicotinic acid;

5-cyclopropyl-2-(2,5-difluoro-3'-methoxybiphenyl-4-ylamino)nicotinic acid;

5-cyclopropyl-2-(3,5-difluoro-3'-(trifluoromethoxy)biphenyl-4-ylamino)nicotinic acid;

2-(2'-chloro-3,5-difluorobiphenyl-4-ylamino)-5-cyclopropylnicotinic acid;

2-(2,3,5,6-tetrafluoro-3'-methoxybiphenyl-4-ylamino)nicotinic acid;

or a pharmaceutically acceptable salt or N-oxide thereof.

Most preferably, the DHODH inhibitor is 2-(3'-Ethoxy-3,5-difluorobiphenyl-4-ylamino)nicotinic acid, 2-(3,5-difluoro-3'-methoxybiphenyl-4-ylamino)nicotinic acid, 2-(3,5-Difluoro-3'-methoxybiphenyl-4-ylamino)-5-methylnicotinic acid, 2-(3'-cyclopropoxy-3,5-difluorobiphenyl-4-ylamino)nicotinic acid or 5-cyclopropyl-2-(3,5-difluoro-3'-(trifluoromethoxy)biphenyl-4-ylamino)nicotinic acid, or a pharmaceutically acceptable salt or N-oxide thereof.

Preferably the active ingredients (a) and (b) form part of a single pharmaceutical composition.

Further provided is a combination as described above which further comprises (c) another compound selected from:
- (i) Anti-TNF-alpha monoclonal antibodies such as Infliximab, Certolizumab pegol, Golimumab, Adalimumab and AME-527 from Applied Molecular Evolution;
- (ii) TNF-alpha Antagonists such as Etanercept, Lenercept, Onercept and Pegsunercept;
- (iii) Calcineurin (PP-2B) Inhibitors/INS Expression Inhibitors such as cyclosporine A, Tacrolimus and ISA-247 from Isotechnika;
- (iv) IL-1 Receptor Antagonists such as Anakinra and AMG-719 from Amgen;
- (v) Anti-CD20 monoclonal antibodies such as Rituximab, Ofatumumab, Ocrelizumab and TRU-015 from Trubion Pharmaceuticals;
- (vi) p38 Inhibitors such as AMG-548 (from Amgen), ARRY-797 (from Array Biopharma), Chlormethiazole edisylate, Doramapimod, PS-540446 (from BMS), SB-203580, SB-242235, SB-235699, SB-281832, SB-681323, SB-856553 (all from GlaxoSmithKline), KC-706 (from Kemia), LEO-1606, LEO-15520 (all from Leo), SC-80036, SD-06 (all from Pfizer), RWJ-67657 (from R.W. Johnson), RO-3201195, RO-4402257 (all from Roche), AVE-9940 (from Aventis), SCIO-323, SCIO-469 (all from Scios), TA-5493 (from Tanabe Seiyaku), and VX-745 and VX-702 (all from Vertex);
- (vii) NF-kappaB (NFKB) Activation Inhibitors such as Sulfasalazine and Iguratimod;
- (viii) A dihydrofolate reductase (DHFR) inhibitor such as Aminopterin and CH-1504 from Chelsea;
- (ix) Janus kinase (JAK) inhibitors, such as CP-690, 550 from Pfizer and INCB-18424, from Incyte;
- (x) MEK inhibitor, such as ARRY-162 from Array;
- (xi) Sphingosine-1 phosphate receptor agonists, such as fingolimod (Novartis);
- (xii) Interferons comprising Interferon beta 1a such as Avonex from Biogen Idec, CinnoVex from CinnaGen and Rebif from Merck Serono, and Interferon beta 1b such as Betaferon from Schering and Betaseron from Berlex;
- (xiii) Immunomodulators such as BG-12 (fumaric acid derivative) from Biogen Idec/Fumapharm AG;
- (xiv) Adenosine aminohydrolase inhibitors such as Cladribine from Merck Serono.

The present invention further provides use of (a) methotrexate and (b) a DHODH inhibitor of the invention for the preparation of a medicament for simultaneous, separate or sequential use in the treatment of a pathological condition or disease susceptible to amelioration by inhibition of dehydroorotate dehydrogenase.

Diseases or disorders in which DHODH inhibition plays a role include without limitation autoimmune diseases, immune and inflammatory diseases, destructive bone disorders, malignant neoplastic diseases, angiogenic-related disorders, viral diseases, and infectious diseases.

Autoimmune diseases which may be prevented or treated include but are not limited to rheumatoid arthritis, psoriatic arthritis, systemic lupus erythematosus, multiple sclerosis, psoriasis, ankylosing spondilytis, Wegener's granulomatosis, polyarticular juvenile idiopathic arthritis, inflammatory bowel disease such as ulcerative colitis and Crohn's disease, Reiter's syndrome, fibromyalgia and type-1 diabetes.

Immune and inflammatory diseases which may be prevented or treated include but are not limited to asthma, COPD, respiratory distress syndrome, acute or chronic pancreatitis, graft versus-host disease, chronic sarcoidosis, transplant rejection, contact dermatitis, atopic dermatitis, allergic rhinitis, allergic conjunctivitis, Behcet syndrome, inflammatory eye conditions such as conjunctivitis and uveitis.

Destructive bone disorders which may be prevented or treated include but are not limited to osteoporosis, osteoarthritis and multiple myeloma-related bone disorder.

Malignant neoplastic diseases that may be prevented or treated include but are not limited to prostate, ovarian and brain cancer.

Agiogenesis-related disorders that may be prevented or treated include but are not limited to hemangiomas, ocular neovascularization, macular degeneration or diabetic retinopathy.

Viral diseases which may be prevented or treated include but are not limited to HIV infection, hepatitis and cytomegalovirus infection.

Infectious diseases which may be prevented or treated include but are not limited to sepsis, septic shock, endotoxic shock, Gram negative sepsis, toxic shock syndrome, Shigellosis and other protozoal infestations such as malaria.

Preferably, the pathological condition or disease is selected from rheumatoid arthritis, psoriatic arthritis, ankylosing spondilytis, multiple sclerosis, Wegener's granulomatosis, systemic lupus erythematosus, psoriasis and sarcoidosis. More preferably the pathological condition or disease is rheumatoid arthritis, psoriatic arthritis or psoriasis. Most preferably it is rheumatoid arthritis.

Also provided is a combination comprising (a) Interferons such as Interferon beta 1a or Interferon beta 1b, and (b) a DHODH inhibitor of the invention, preferably a DHODH inhibitor of formula (I).

Also provided is the use of a combination comprising (a) Interferons such as Interferon beta 1a or Interferon beta 1b, and (b) a DHODH inhibitor of the invention, preferably a DHODH inhibitor of formula (I) for the preparation of a medicament for simultaneous, separate or sequential use for the treatment of multiple scleroris.

Also provided is a product comprising (a) methotrexate and (b) a DHODH inhibitor of the invention, as a combined preparation for simultaneous, separate or sequential use in the treatment of a human or animal patient suffering from or susceptible to a pathological condition or disease as defined above. Said product may optionally further comprise an active compound (c), as defined above.

Also provided is a kit of parts comprising (b) a DHODH inhibitor of the invention together with instructions for simultaneous, separate or sequential use in combination with (a) methotrexate, for the treatment of a human or animal patient suffering from or susceptible to a pathological condition or disease as defined above. Said kit may optionally further comprise an active compound (c), as defined above.

Also provided is a package comprising (b) a DHODH inhibitor of the invention and (a) methotrexate, for simultaneous, separate or sequential use in the treatment of a pathological condition or disease as defined above. Said package may optionally further comprise an active compound (c), as defined above.

Also provided is a use of (b) a DHODH inhibitor of the invention for the preparation of a medicament, for use in combination with (a) methotrexate, for the treatment of a pathological condition or disease as defined above.

Also provided is a use of (a) methotrexate, for the preparation of a medicament, for use in combination with (b) a DHODH inhibitor of the invention, for the treatment of a pathological condition or disease as defined above.

Also provided is a use as defined above wherein the methotrexate (a) is for administration at a dosage regime which involves administration of 0.015 to 3 mg/kg/week of methotrexate and the DHODH inhibitor (b) is for administration at a dosage regime which involves administration of 0.03 to 30 mg/kg/day of DHODH inhibitor.

Typically the medicament is for use in treating a human or animal patient suffering or susceptible to hepatic impairment or a condition that would be aggravated by hepatotoxicity. More typically, the said human or animal patient is suffering from liver fibrosis, hepatitis (typically hepatitis A to G), cirrhosis (typically caused by alcoholism) or liver cancer.

In one embodiment of the present invention, the combination, product, kit of parts or package comprises (b) a DHODH inhibitor of the invention, and (a) methotrexate, as the sole active components.

The fact that the DHODH inhibitors of the invention have reduced hepatic side effects is a finding of the invention. The present invention therefore also provides the use of a DHODH inhibitor of the invention, as defined above, in the manufacture of a medicament for use in treating or preventing a pathological condition or disease, as defined above, in a human or animal patient which is suffering from or susceptible to hepatic impairment or a condition that would be aggravated by hepatotoxicity, as defined above.

Also provided is a method of treating a human or animal patient suffering from or susceptible to a pathological condition or disease as defined above, which method comprises simultaneously, separately or sequentially administering to said human or animal patient a therapeutically effective amount of (a) methotrexate and (b) a DHODH inhibitor as defined above. Preferably in said method, (a) methotrexate and (b) the DHODH inhibitor are the sole active components.

Also provided is a method of treating a human or animal patient suffering from or susceptible to a pathological condition or disease as defined above, wherein the human or animal patient is suffering from or susceptible to hepatic impairment or a condition that would be aggravated by hepatotoxicity as defined above, which method comprises administering to said human or animal patient a therapeutically effective amount of a DHODH inhibitor as defined above.

Also provided is a combination as defined above for use in treating a pathological condition or disease as defined above.

Also provided is a DHODH inhibitor as defined above for use in treating a human or animal patient suffering from or susceptible to a pathological condition or disease as defined above, wherein the human or animal patient is suffering from or susceptible to hepatic impairment or a condition that would be aggravated by hepatotoxicity, as defined above.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc); topically (as creams, ointments, lotions, nasal sprays or aerosols, etc); by injection (subcutaneous, intradermic, intramuscular, intravenous, etc.) or by inhalation (as a dry powder, a solution, a dispersion, etc).

The active compounds in the combination may be administered together in the same pharmaceutical composition or in different compositions intended for separate, simultaneous, concomitant or sequential administration by the same or a different route.

The combinations of the invention may conveniently be presented in unit dosage form and may be prepared by any of the methods well known in the art of pharmacy.

Combinations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A syrup formulation will generally consist of a suspension or solution of the compound or salt in a liquid carrier for example, ethanol, peanut oil, olive oil, glycerine or water with flavouring or colouring agent.

Where the combination is in the form of a tablet, any pharmaceutical carrier routinely used for preparing solid formulations may be used. Examples of such carriers include magnesium stearate, talc, gelatine, acacia, stearic acid, starch, lactose and sucrose.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Where the combination is in the form of a capsule, any routine encapsulation is suitable, for example using the aforementioned carriers in a hard gelatine capsule. Where the composition is in the form of a soft gelatine capsule any pharmaceutical carrier routinely used for preparing dispersions or suspensions may be considered, for example aqueous gums, celluloses, silicates or oils, and are incorporated in a soft gelatine capsule.

The combination may be in the form of a dry powder composition for topical delivery to the lung by inhalation. Dry powder compositions may, for example, be presented in capsules and cartridges of for example gelatine or blisters of for example laminated aluminium foil, for use in an inhaler or insufflator. Formulations generally contain a powder mix for inhalation of the compound of the invention and a suitable powder base (carrier substance) such as lactose or starch. Use of lactose is preferred. Each capsule or cartridge may generally contain between 2 µg and 150 µg of each therapeutically active ingredient. Alternatively, the active ingredient (s) may be presented without excipients.

Packaging of the formulation for inhalation may be carried out by using suitable inhaler devices such as the Novolizer® SD2FL or Genuair® which are described in the following patent applications: WO 97/000703, WO 03/000325 and WO 03/061742.

The combination may be in the form of a composition for nasal delivery. Typical compositions for nasal delivery include those mentioned above for inhalation and further include non-pressurized compositions in the form of a solution or suspension in an inert vehicle such as water optionally in combination with conventional excipients such as buffers, anti-microbials, tonicity modifying agents and viscosity modifying agents which may be administered by nasal pump.

Typical dermal and transdermal formulations comprise a conventional aqueous or non-aqueous vehicle, for example a cream, ointment, lotion or paste or are in the form of a medicated plaster, patch or membrane.

Preferably the combination is in unit dosage form, for example a tablet, capsule or metered aerosol dose, so that the patient may administer a single dose.

The amount of each active which is required to achieve a therapeutic effect will, of course, vary with the particular active, the route of administration, the subject under treatment, and the particular disorder or disease being treated.

Typically all active agents in the combination are administered at the same time, or very close in time. Alternatively, one or two actives could be taken in the morning and the other (s) later in the day. Or in another scenario, one or two actives could be taken twice daily and the other (s) once daily, either at the same time as one of the twice-a-day dosing occurred, or separately. Preferably at least two, and more preferably all, of the actives would be taken together at the same time. Preferably, at least two, and more preferably all actives would be administered as an admixture.

Preferably the drug combination of the invention is for administration as a dosage regime which involves administration of (i) 0.015 to 3 mg/kg/week of methotrexate, more preferably 0.07 to 0.7 mg/kg/week of methotrexate and most preferably 0.15 to 0.35 mg/kg/week of methotrexate, and (ii) 0.03 to 30 mg/kg/day of DHODH inhibitor, more preferably 0.07 to 14 mg/day of DHODH inhibitor and most preferably 0.15 to 0.3 mg/kg/day of DHODH inhibitor.

EXAMPLES

Example 1

Inhibition of Human DHODH Activity Assay

DHODH activity and its inhibition were studied using a chromogen reduction assay with DCIP (2,6-dichlorophenol-indophenol). The substrate oxidation (Dihydroorotate, L-DHO), as well as cosubstrate reduction (coenzyme Q, CoQ) is coupled to the chromogen reduction, hence enzymatic activity results in a loss of chromogen absorbance at 600 nm.

Enzyme extracts (8 µl, ~1.5 µg of human protein) were incubated in 96-well plates. The assay mixture (200 µl) contained 200 µM CoQD, 100 µM L-DHO, 120 µM DCIP in the assay buffer (100 mM HEPES pH 8.0, 150 mM NaCl, 10% Glicerol, 0.05% Triton X-100) and 2 µl of test compound. The compounds were dissolved in DMSO at a stock concentration of 1 mM, and tested at different concentrations varying from 10 µM to 1 pM to calculate an $IC_{50}$ (concentration of inhibitor required for 50% of inhibition).

The reaction was initiated by adding the enzyme and then incubated for 10 min at room temperature before measuring DCIP reduction by counting a decrease in absorbance at 600 nm using standard instrumentation (Spectramax).

All reactions were carried out in duplicate and graphs, determining $IC_{50}$ values for each compound, were plotted using the ABase software.

Table 1 shows the activities in human DHODH inhibition assay of some compounds of the present invention (compounds from the list indicated previously) showing that these compounds are potent DHODH inhibitors.

TABLE 1

| Compound No. | hDHODH $IC_{50}$ (nM) |
| --- | --- |
| 2 | 200 |
| 6 | 88 |
| 13 | 150 |

TABLE 1-continued

| Compound No. | hDHODH $IC_{50}$ (nM) |
| --- | --- |
| 17 | 90 |
| 19 | 19 |
| 20 | 15 |
| 21 | 19 |
| 23 | 14 |
| 24 | 200 |
| 33 | 110 |
| 34 | 33 |
| 35 | 12 |
| 37 | 99 |
| 40 | 12 |
| 42 | 23 |
| 45 | 53 |
| 47 | 17 |
| 48 | 5 |
| 50 | 6 |
| 52 | 4 |
| 54 | 5 |
| 56 | 6 |
| 57 | 4 |
| 58 | 8 |
| 60 | 3 |
| 61 | 11 |

Example 2

Reduced Hepatotoxicity

Acute hepatotoxicity assays were performed in Swiss mice. Animals received a single administration of either vehicle, or 100 mg/kg of teriflunomide or a compound of the present invention (compounds from the list indicated previously) by intraperitoneal route. Twenty-four hours later, animals were sacrificed and the levels of liver markers AST (aspartate aminotransferase), ALT (alanine aminotransferase) and BIL (total bilirubin) in plasma were determined.

TABLE 2

Plasma levels of liver markers of mice after administration of 100 mg/kg of the compound, 100 mg/kg Teriflunomide or vehicle (IU: International Units).

| Compound No. | ALT (IU/l) | AST (IU/l) | BIL (mg/dl) |
| --- | --- | --- | --- |
| 1 | 99 | 84 | 0.03 |
| 2 | 35 | 57 | 0 |
| 3 | 52 | 83 | 0.01 |
| 4 | 70 | 108 | 0.05 |
| 19 | 60 | 92 | 0.05 |
| 20 | 73 | 95 | 0 |
| 23 | 35 | 72 | 0 |
| 47 | 66 | 91 | 0.14 |
| 48 | 44 | 95 | 0.08 |
| 57 | 60 | 109 | 0.06 |
| Vehicle | 55 | 78 | 0.05 |
| Teriflunomide | 423 | 542 | 0.5 |

As it can clearly seen from Table 2, Teriflunomide-treated mice showed a dramatic increase in the three liver markers compared to vehicle-treated mice, clearly indicating a high hepatotoxicity, whereas the DHODH inhibitors according to the present invention did not cause a significant increase in any of the parameters measured Example 3

Efficacy Assay in Adjuvant-induced Arthritis of the Combination Product of the Present Invention The effect of DHODH inhibitor compounds were tested in combination with methotrexate (0.05 mg/Kg/day) in the rat adjuvant-induced arthritis model (AIA) in animals with established disease (curative protocol). Briefly, Complete Freund Adjuvant (CFA) was injected into the left hind footpad of Wistar rats, and 10 days later the swelling of the two rear paws was measured with a plethysmometer. Rats exhibiting a similar degree of inflammation in both paws were randomized into treatment groups (n=7 per group). Compounds were administered orally once a day for 10 days and paw volumes were determined every two days up to day 21.

TABLE 3

Effects of compound A (3 mg/Kg/day), Methotrexate (0.05 mg/Kg/day) and their combination on the inhibition of paw inflammation in arthritic rats. Results are expressed as the mean inhibition of the inflammation measured as the area under the curve (AUC) of the right paw volumes in the period comprised between days 10 and 21 post-induction.
The percentage of inhibition for every group was calculated versus values from vehicle-treated rats. Results are the mean of two independent experiments, each with 5-6 animals per group.

| Treatment | % inhibition of the inflammation (AUC) Right paw |
|---|---|
| Compound A (3 mg/Kg) | 41 |
| MTX (0.05 mg/Kg) | 37 |
| Compound A (3 mg/Kg) + MTX (0.05 mg/Kg) | 55 |

Results from Table 3 show that compound A of the present invention inhibits the inflammation caused by experimental arthritis in rats. Furthermore, the co-administration of MTX and compound A resulted in an increased efficacy (34%) versus compound A alone, thus indicating the feasibility of administering the compound in patients treated with MTX.

TABLE 4

Effects of Teriflunomide (3 mg/Kg/day), Methotrexate (0.05 mg/Kg/day) and their combination on the inhibition of paw inflammation in arthritic rats. The results are expressed as the mean inhibition of inflammation measured as the area under the curve (AUC) of the right paw volumes in the period comprised between days 10 and 21 post-induction.
The percentage of inhibition for every group was calculated versus values from vehicle-treated rats.
Results are the mean of one experiment with 6 animals.

| Treatment | % AUC inhibition right paw |
|---|---|
| Teriflunomide (3 mg/Kg) | 56 |
| MTX (0.05 mg/Kg) | 24 |
| Teriflunomide (3 mg/Kg) + MTX (0.05 mg/Kg) | 61 |

The co-administration of MTX and Teriflunomide resulted in an increased efficacy (9%) versus Teriflunomide alone.

From the experimental results, it can be concluded that the DHODH inhibitor compounds of the present invention show antiarthritic effect alone as well as in combination with MTX, like teriflunomide, but a clearly diminished hepatotoxic potencial, making the combination of the present invention, i.e. (a) MTX and (b) a DHODH inhibitor of the invention, more attractive from the safety profile point of view.

The invention claimed is:

1. A combination comprising (a) methotrexate, and (b) a non-hepatotoxic DHODH inhibitor, wherein the non-hepatotoxic DHODH inhibitor is chosen from:
   2-(3'-ethoxy-3,5-difluorobiphenyl-4-ylamino)nicotinic acid;
   2-(3,5-difluoro-3'-methoxybiphenyl-4-ylamino)nicotinic acid;
   2-(3'-cyclopropoxy-3,5-difluorobiphenyl-4-ylamino) nicotinic acid;
   2-(3,5-difluoro-3'-methoxybiphenyl-4-ylamino)-5-methylnicotinic acid;
   or a pharmaceutically acceptable salt or N-oxide thereof.

2. The combination according to claim 1, wherein the non-hepatotoxic DHODH inhibitor is 2-(3'-ethoxy-3,5-difluorobiphenyl-4-ylamino)nicotinic acid or a pharmaceutically acceptable salt or N-oxide thereof.

3. The combination according to claim 1, wherein the non-hepatotoxic DHODH inhibitor is 2-(3,5-difluoro-3'-methoxybiphenyl-4-ylamino)nicotinic acid or a pharmaceutically acceptable salt or N-oxide thereof.

4. The combination according to claim 1, wherein the non-hepatotoxic DHODH inhibitor is 2-(3'-cyclopropoxy-3,5-difluorobiphenyl4-ylamino)nicotinic acid or a pharmaceutically acceptable salt or N-oxide thereof.

5. The combination according to claim 1, wherein the non-hepatotoxic DHODH inhibitor is 2-(3,5-difluoro-3'-methoxybiphenyl-4-ylamino)-5-methylnicotinic acid or a pharmaceutically acceptable salt or N-oxide thereof.

6. The combination according to claim 1, wherein the active ingredients (a) methotrexate, and (b) non-hepatotoxic DHODH inhibitor form part of a single pharmaceutical composition.

7. The combination according to claim 1, further comprising at least one compound (c) chosen from:
   (i) Anti-TNF-alpha monoclonal antibodies;
   (ii) TNF-alpha Antagonists;
   (iii) Calcineurin (PP-2B) Inhibitors/INS Expression Inhibitors;
   (iv) IL-1 Receptor Antagonists;
   (v) Anti-CD20 monoclonal antibodies;
   (vi) p38 Inhibitors;
   (vii) NF-kappaB (NFKB) Activation Inhibitors;
   (viii) Another dihydrofolate reductase (DHFR) inhibitors;
   (ix) Janus kinase (JAK) inhibitors;
   (x) MEK inhibitors; and
   (xi) Sphingosine-1 phosphate receptor agonists;
   (xii) Interferons comprising Interferon beta 1a, and interferons comprising Interferon beta 1 b;
   (xiii) Inmunomodulators; and
   (xiv) Adenosine aminohydrolase inhibitors.

8. A product comprising (a) methotrexate, and (b) a non-hepatotoxic DHODH inhibitor according to claim 1, as a combined preparation for simultaneous, separate or sequential administration.

9. The product according to claim 8, further comprising at least one compound (c) chosen from:
   (i) Anti-TNF-alpha monoclonal antibodies;
   (ii) TNF-alpha Antagonists;
   (iii) Calcineurin (PP-2B) Inhibitors/INS Expression Inhibitors;
   (iv) IL-1 Receptor Antagonists;
   (vi) p38 Inhibitors;
   (vii) NF-kappaB (NFKB) Activation Inhibitors;
   (viii) Another dihydrofolate reductase (DHFR) inhibitors;
   (ix) Janus kinase (JAK) inhibitors;
   (x) MEK inhibitors;
   (xv) Interferons comprising Interferon beta 1a, and interferons comprising Interferon beta 1 b;
   (xvi) Inmunomodulators; and
   (xvii) Adenosine aminohydrolase inhibitors.

10. A kit of parts comprising (b) a non-hepatotoxic DHODH inhibitor according to claim 1, together with instructions for simultaneous, separate or sequential administration in combination with (a) methotrexate.

11. The kit according to claim 10, further comprising at least one compound (c) chosen from:
- (i) Anti-INF-alpha monoclonal antibodies;
- (ii) TNF-alpha Antagonists;
- (iii) Calcineurin (PP-2B) Inhibitors/INS Expression Inhibitors;
- (iv) IL-1 Receptor Antagonists;
- (vi) p38 Inhibitors;
- (vii) NF-kappaB (NFKB) Activation Inhibitors;
- (viii) Another dihydrofolate reductase (DHFR) inhibitors;
- (ix) Janus kinase (JAK) inhibitors;
- (x) MEK inhibitors;
- (xviii) Interferons comprising Interferon beta 1a, and interferons comprising Interferon beta 1b;
- (xix) Inmunomodulators; and
- (xx) Adenosine aminohydrolase inhibitors.

12. A package comprising (b) a non-hepatotoxic DHODH inhibitor according to claim 1, and (a) methotrexate, for simultaneous, separate or sequential administration.

13. The package according to claim 12, further comprising at least one compound (c) chosen from:
- (i) Anti-TNF-alpha monoclonal antibodies;
- (ii) TNF-alpha Antagonists;
- (iii) Calcineurin (PP-2B) Inhibitors/INS Expression Inhibitors;
- (iv) 1L-1 Receptor Antagonists;
- (vi) p38 Inhibitors;
- (vii) NF-kappaB (NFKB) Activation Inhibitors;
- (viii) Another dihydrofolate reductase (DHFR) inhibitors;
- (ix) Janus kinase (JAK) inhibitors;
- (x) MEK inhibitors;
- (xxi) Interferons comprising Interferon beta 1a, and interferons comprising Interferon beta 1b;
- (xxii) Inmunomodulators; and
- (xxiii) Adenosine aminohydrolase inhibitors.

14. A method for preparing a medicament, comprising: combining (b) a non-hepatotoxic DHODH inhibitor according to claim 1, with (a) methotrexate.

15. A method of treating a human or animal patient suffering from a disease chosen from the group consisting of rheumatoid arthritis, psoriatic arthritis, ankylosing spondylitis, multiple sclerosis, and Wegener's granulomatosis, comprising simultaneously, separately or sequentially administering to the human or animal patient a therapeutically effective amount of (a) methotrexate and (b) a non-hepatotoxic DHODH inhibitor according to the combination of claim 3, wherein the disease is ameliorated by inhibition of dihydroorotate dehydrogenase.

16. A method of treating a human or animal patient suffering from a disease chosen from the group consisting of rheumatoid arthritis, psoriatic arthritis, ankylosing spondylitis, multiple sclerosis, and Wegener's granulomatosis, comprising simultaneously, separately or sequentially administering to the human or animal patient a therapeutically effective amount of (a) methotrexate and (b) a non-hepatotoxic DHODH inhibitor according to the combination of claim 3, wherein the administering of the combination of claim 3 is effective for reducing hepatotoxicity resulting from liver fibrosis, hepatitis, cirrhosis, or liver cancer of the human or animal patient.

17. A method according to claim 15, wherein the (a) methotrexate is administered at a dose of 0.015 to 3 mg/kg/week, and the (b) non-hepatotoxic DHODH inhibitor is administered at a dose of 0.03 to 30 mg/kg/day.

* * * * *